United States Patent [19]

Hall et al.

[11] Patent Number: 5,006,542
[45] Date of Patent: Apr. 9, 1991

[54] ARYLTHIOALKYLPHENYL CARBOXYLIC ACIDS, DERIVATIVES THEREOF, COMPOSITIONS CONTAINING SAME AND METHOD OF USE

[75] Inventors: Steven E. Hall, Trenton; Philip D. Stein, Princeton, both of N.J.

[73] Assignee: E. R. Squibb & Sons, Inc., Princeton, N.J.

[21] Appl. No.: 264,939

[22] Filed: Oct. 31, 1988

[51] Int. Cl.$^5$ .................... C07C 321/00; A61K 31/41
[52] U.S. Cl. ...................... 514/381; 514/533;
514/539; 514/543; 514/562; 514/569; 514/571;
514/602; 514/604; 514/605; 548/252; 548/253;
560/10; 560/11; 560/12; 562/427; 562/429;
562/430; 564/81; 564/91; 564/99
[58] Field of Search .............. 560/11, 12, 10;
562/429, 430, 427; 514/543, 571, 381, 604, 605,
533, 539, 562, 569, 602; 564/91, 81, 99;
548/252, 253

[56] References Cited

U.S. PATENT DOCUMENTS

| 4,258,058 | 3/1981 | Witte | 424/309 |
| 4,443,477 | 4/1984 | Witte | 424/319 |
| 4,552,616 | 6/1988 | Hall | 514/510 |
| 4,752,613 | 6/1988 | Floyd | 514/438 |
| 4,755,524 | 7/1988 | Mueller | 560/11 |

FOREIGN PATENT DOCUMENTS

| 56172A2 | 7/1982 | European Pat. Off. . | |
| 223593 | 5/1987 | European Pat. Off. . | |
| 242518A1 | 10/1987 | European Pat. Off. . | |
| 253257A2 | 1/1988 | European Pat. Off. . | |
| 261539A2 | 3/1988 | European Pat. Off. . | |
| 301421 | 2/1989 | European Pat. Off. | 560/11 |
| 3622865A1 | 1/1988 | Fed. Rep. of Germany . | |
| 3629929A1 | 10/1988 | Fed. Rep. of Germany . | |
| 88095 | 8/1988 | Portugal . | |

Primary Examiner—Michael L. Shippen
Attorney, Agent, or Firm—Burton Rodney

[57] ABSTRACT

Arylthioalkylphenylcarboxylic acids are provided which have the structure

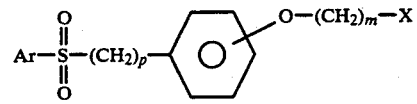

wherein Ar represents an aryl group including phenyl or naphthyl which may or may not include one or more substituents, X is COOR where R is hydrogen, alkali metal, or lower alkyl, or X is 5-tetrazolyl or

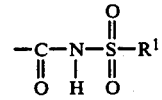

where $R^1$ is lower alkyl or aryl, p is 1 to 5, and m is 1 to 4. These compounds are cardiovascular agents which exhibit thromboxane antagonist activity and thus are useful in the treatment of thrombotic and vasopastic diseases.

7 Claims, No Drawings

ARYLTHIOALKYLPHENYL CARBOXYLIC ACIDS, DERIVATIVES THEREOF, COMPOSITIONS CONTAINING SAME AND METHOD OF USE

FIELD OF THE INVENTION

The present invention relates to arylthioalkylphenyl carboxylic acids and derivatives thereof which are useful in the treatment of thrombotic and/or vasospastic disease.

BACKGROUND OF THE INVENTION

U.S. Pat. No. 4,258,058 discloses phenoxyalkyl carboxylic acids which inhibit thrombocyte aggregation and depress serum lipids and have the structure

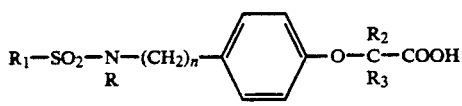

wherein
R is hydrogen or lower alkyl;
$R_1$ is an alkyl or aryl, aralkyl or aralkenyl radical, the aryl moiety of which can be substituted one or more times by halogen, hydroxyl, trifluoromethyl or lower alkyl, alkoxy or acyl;
$R_2$ and $R_3$, which can be the same or different, are hydrogen or lower alkyl and
n is 0, 1, 2 or 3;
as well as the physiologically acceptable salts, esters and amides thereof.

U.S. Pat. No. 4,443,477 discloses sulphonamidophenyl carboxylic acids which inhibit thrombocyte aggregation and depress serum lipids and have the structure

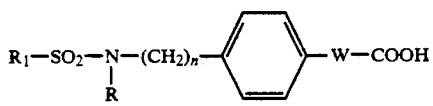

wherein
R is a hydrogen atom or a lower alkyl radical;
$R_1$ is an alkyl radical or an aryl, aralkyl or aralkenyl radical, the aryl moiety of which in each case can be optionally substituted one or more times by hydroxyl, halogen, trifluoromethyl, lower alkyl or alkoxy or by acyl, carboxy or alkoxycarbonyl;
n is 1, 2 or 3; and
W is a bond or an unbranched or branched divalent aliphatic hydrocarbon chain, which is either saturated or contains a double bond, as well as the physiologically acceptable salts, esters and amides thereof.

U.S. Pat. No. 4,752,616 discloses alkylthioalkylphenyl carboxylic acids which are thromboxane receptor antagonists of the structure

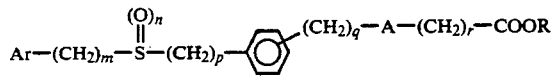

wherein
Ar represents aryl which is unsubstituted or optionally substituted with one, two or three of the following: halogen, lower alkyl, lower alkoxy, phenyl, hydroxy, alkanoyl, aroyl, alkylamino, alkoxycarbonyl or carboxy;
A is

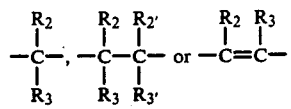

wherein $R_2$ and $R_3$, and $R_{2'}$ and $R_{3'}$ may be the same or different and are independently selected from hydrogen or lower alkyl,
R is hydrogen, alkali metal (such as Na, K or Li) or lower alkyl,
n is 0, 1 or 2,
m is 0, 1, 2 or 3,
p is 1 to 5,
q is 0, 1, 2 or 3, and
r is 0, 1, 2 or 3.
The $(CH_2)_m$, $(CH_2)_p$, $(CH_2)_q$ and $(CH_2)_r$ groups may be optionally substituted with one or two lower alkyl and/or one or two lower alkoxy substituents.
The $-(CH_2)_q-A-(CH_2)_r-COOR$ group may be attached at the ortho, meta or para position, with para being preferred.

European patent application 0056172 A2 discloses phenoxy- and thiophenoxy compounds, methods for their preparation and pharmaceutical formulations containing them having the formula I

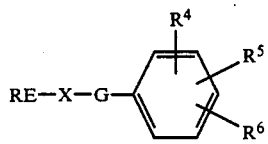

in which
R is a group of formula II

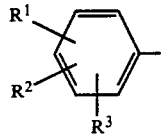

$R^1$, $R^2$ and $R^3$, which may be the same or different each represent hydrogen, alkyl, alkenyl, alkenyloxy, halogen, alkoxy, alkanoyl or hydroxy,
one or more of $R^4$, $R^5$ and $R^6$ represents alkyl, alkanoyl, alkenyl, —COOH or —ACOOH where A represents Y, OY or SY and Y represents a —CH=CH—, methylene, ethylene or 1,3-propylene chain, and the remainder of $R^4$, $R^5$ and $R^6$ represent hydrogen,
X represents a hydrocarbon chain having from 2 to 7 carbon atoms optionally substituted by hydroxy,
E represents —S—, —O—, or —CH₂—, and
G represents —S— or —O—, (with various exceptions) and pharmaceutically acceptable derivatives of those compounds containing an acidic function.

These compounds are disclosed as antagonists of the slow reacting substance of anaphylaxis.

U.S. Pat. No. 4,752,613 to Floyd et al discloses compounds of the structure

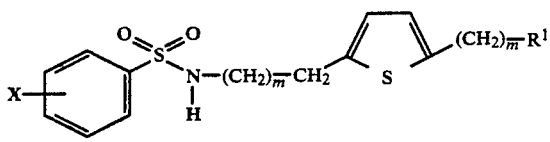

wherein X is halogen, lower alkyl, arylalkyl, alkoxy or hydroxy; wherein the phenyl ring is mono or disubstituted, $R^1$ is —COOH or

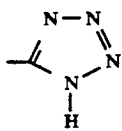

or

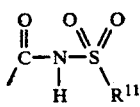

wherein $R^{11}$ is lower alkyl or aryl and n and m are independently zero, one, two or three which are potent thromboxane $A_2$ receptor antagonists.

DESCRIPTION OF THE INVENTION

In accordance with the present invention, arylthioalkylphenyl carboxylic acid compounds are provided having the following structural formula:

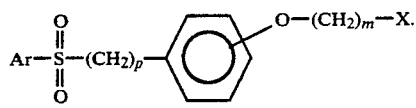      I wherein Ar represents aryl which is unsubstituted or optionally substituted with one, two or three of the following: halogen, lower alkyl, lower alkoxy, phenyl, hydroxy, alkanoyl, aroyl, alkylamino, alkoxycarbonyl or carboxy; wherein X is COOR and R is hydrogen, alkali metal (such as Na, K or Li), or lower alkyl, or X is 5-tetrazolyl or

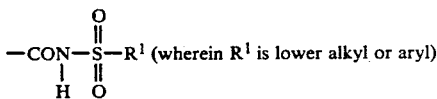

p is 1 to 5, m is 1 to 4.

The $(CH_2)_p$ and $(CH_2)_m$ groups may be optionally substituted with one or two lower alkyl and/or one or two lower alkoxy substituents.

The —O—$(CH_2)_m$—COOR group may be attached at the ortho, meta or para position.

The term "lower alkyl" or "alkyl" as employed herein by itself or as part of another group includes both straight and branched chain hydrocarbon radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including one or two halo-substituents, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), and/or 1 or 2 lower alkoxy groups.

The term "aralkyl", "aryl-alkyl" or "aryl-lower alkyl" as used herein by itself or as part of another group refers to lower alkyl groups as discussed above having an aryl substituent, such as benzyl.

The term "alkanoyl" and "aroyl" refer to a lower alkyl group linked to a carbonyl group or an aryl group linked to a carbonyl group.

The term "halogen" or "halo" as used herein by itself or as part of another group refers to chlorine, bromine, fluorine or iodine, with chlorine being preferred.

The terms "$(CH_2)_p$", and $(CH_2)_m$ where present include a straight or branched chain radical having 1 to 5 carbons in the normal chain in the case of "$(CH_2)_p$" and 1 to 4 carbons in the normal chain in the case of "$(CH_2)_m$", and may contain one or more lower alkyl and/or lower alkoxy substitutents. Examples of $(CH_2)_p$, and $(CH_2)_m$ groups include

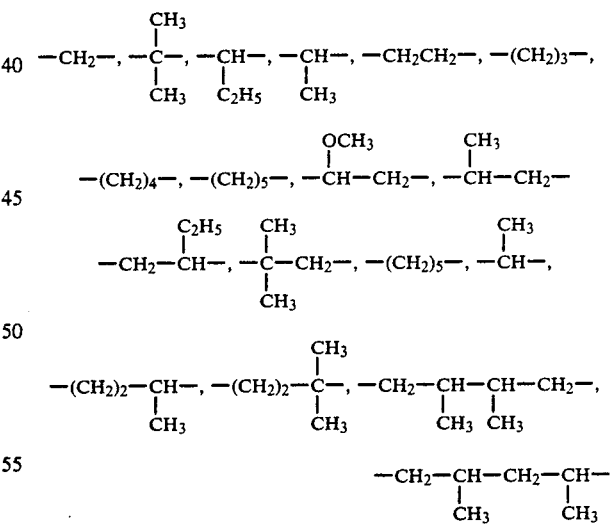

and the like.

Preferred are those compounds of the invention wherein Ar is halophenyl, such as p—Cl—$C_6H_4$—, $(CH_2)_p$ is $(CH_2)_3$.

The various compounds of the invention may be prepared as outlined below.

Compounds of the invention where p is 1 to 5 may be prepared starting with the mercaptan A Ar-SH                                          A which is alkylated by treating A with a strong base such as an alkali metal alkoxide like potassium t-butoxide, sodium methoxide or sodium ethoxide and alkylating agent B

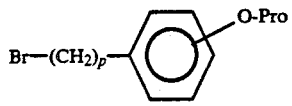  B where Pro represents a protected alcohol group such as

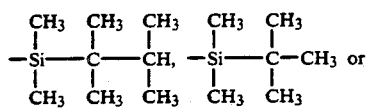

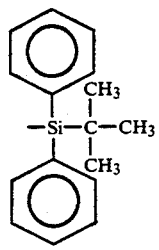

in the presence of an inert organic solvent like tetrahydrofuran, dimethyl sulfoxide or ethanol to form the sulfide compound II

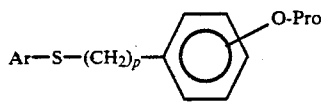  II

The above reaction is carried out at a temperature within the range of from about 20 to about 80° C. employing a molar ratio of A:base within the range of from about 0.8:1 to about 3:1 and preferably from about 1:1 to about 1.5:1, and a molar ratio of B:A within the range of from about 0.8:1 to about 1.2:1 and preferably from about 0.9:1 to about 1.1:1.

The sulfide II is oxidized to the corresponding sulfone III by oxidizing sulfide compound II employing as an oxidizing agent, such as Oxone® (DuPont, 2KHSO$_5$·KHSO$_4$·K$_2$SO$_4$) employing a molar ratio of II:oxidizing agent of within the range of from about 1:2 to about 1:6 and preferably from about 1:3 to about 1:5 to form sulfone III

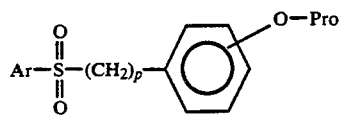  III

The sulfone III may be deprotected by subjecting III to basic hydrolysis by treatment with a base such as lithium hydroxide, sodium hydroxide or potassium hydroxide in the presence of water and an inert solvent such as tetrahydrofuran, to form the corresponding phenol IV.

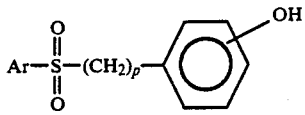  IV

The phenol IV is then alkylated by treating a solution of IV as an inert solvent such as tetrahydrofuran, at a temperature of within the range of from about −10° C. to about 10° C. with a base such as an alkali metal alkoxide like potassium t-butoxide, sodium methoxide or sodium ethoxide and alkylating agent C

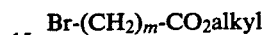

Br-(CH$_2$)$_m$-CO$_2$alkyl    C to form the ester of the invention IA

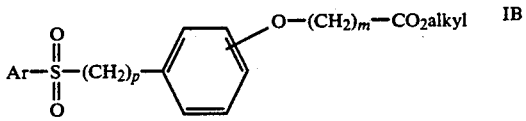  IB

The ester IA may be converted to the alkali metal salt thereof of the invention IB by subjecting IA to basic hydrolysis by treatment with a base such as lithium hydroxide, sodium hydroxide or potassium hydroxide to form the corresponding alkali metal salt IB

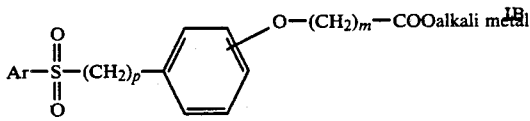  IB

The salt IB may be converted to acid IC by neutralization with an acid such as dilute hydrochloric acid or oxalic acid to form IC.

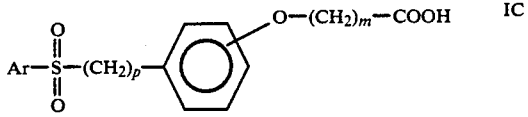  IC

In an alternative process, compounds of formula I wherein p is 2 to 5, that is

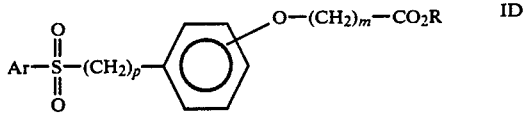  ID p = 2 to 5 may be prepared by alkylating sulfone D

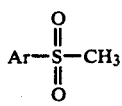  D by treating a solution of D at a temperature within the range of from about −10° C. to about 10° C. in an inert organic solvent such as tetrahydrofuran or ether with a lithiated strong base such as an alkyl lithium compound like n-butyllithium, lithium diisopropylamide or lithium bistrimethylsilylamide in an inert organic solvent such as hexane, ether or THF, cooling the resulting solution to from about −80° C. to about −50° C. and reacting same with a solution of protected compound E

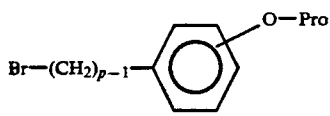

or the like in an inert organic solvent such as tetrahydrofuran or ether to form protected sulfone IIIA

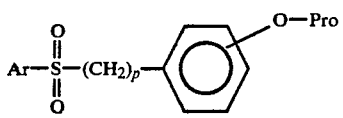

(where p = 2 to 5)

Other known alcohol protecting groups may be employed which may then be removed in a separate step prior to oxidation. The above reaction is carried out employing a molar ratio of D:base of within the range of from about 1.4:1 to about 0.9:1 and preferably from about 1.1:1 to about 1:1 and a molar ratio of D:E of within the range of from about 4:1 to about 1:1 and preferably from about 2:1 to about 1.5:1.

The protected sulfone IIIA may then be converted to the sulfone compounds of the invention where p is 2 to 5 employing procedures set out hereinbefore regarding conversion of sulfone III to the compounds of the invention.

Compounds of the invention wherein

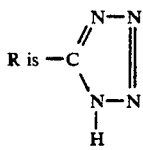

may be prepared starting with phenol IV which is treated with nitrile F

Br(CH$_2$)$_m$-CN  F in the presence of base such as potassium t-butoxide or sodium hydride-dimethyl sulfoxide employing a molar ratio of IV:F of within the range of from about 1:1 to about 0.5:1 to form sulfone compound V

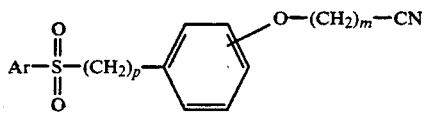

which is treated with an inorganic azide such as sodium azide and ammonium chloride in the presence of a polar solvent such as dimethyl formamide at a temperature of within the range of from about 110° to about 140° C. to form the tetrazole IE.

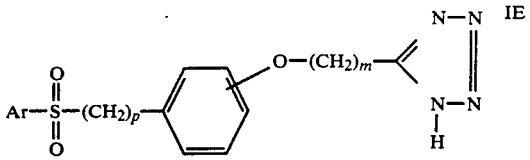

Compounds of the invention wherein X is

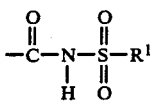

may be prepared by treating acid of the invention IC with coupling reagent such as carbonyldiimidazole (CDI) or 1-(3-dimethylaminopropyl)-3-ethyl-carbodiimide and an alkyl or arylsulfonamide in the presence of an amine such as 4-dimethylaminopyridine and an inert solvent such as tetrahydrofuran at a temperature within the range of from about 0 to about 50° C. employing a molar ratio of IC:coupling reagent of within the range of from about 0.9:1 to about 1.1:1 and a molar ratio of IC:sulfonamide of within the range of from about 0.8:1 to about 1:1 to form the sulfonamide IF of the invention

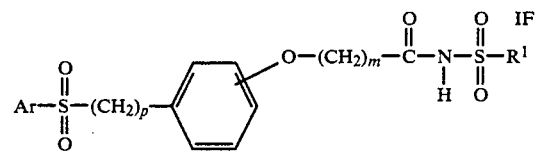

The starting material B where p is 3, 4 or may be prepared starting with protected aryl bromide compound G

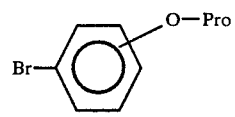

which is added to a mixture of magnesium and I$_2$ in an inert organic solvent such as tetrahydrofuran under an inert atmosphere such as argon to form a Grignard solution. The Grignard solution is added to a stirred solution of dibromoalkane H Br-(CH$_2$)$_p$-Br  H and Li$_2$CuCl$_4$ in the presence of an inert organic solvent such as tetrahydrofuran and under an inert atmosphere such as argon to form B.

The starting compound E may be prepared from alcohol J by a bromination reaction, for example, by treatment of alcohol J at reduced temperatures (−10° to 10° C.) with triphenylphosphine dibromide in an inert solvent such as benzene or toluene to provide bromide E.

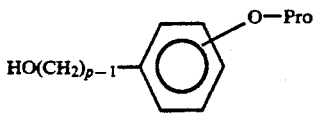

The compounds of this invention are cardiovascular agents useful as platelet aggregation inhibitors, e.g., for treatment of thrombotic disease, such as coronary or cerebral thromboses. In addition, the compounds of the invention are useful in inhibiting bronchoconstriction such as associated with asthma and airways hyperactivity. They are also selective thromboxane $A_2$ receptor antagonists, e.g., having a vasodilatory effect for treatment of myocardial ischemic disease, such as angina pectoris.

In addition, the compounds of the invention may be useful in improving post-ischemic myocardial dysfunction, for example, decreased contractile dysfunction, decrease in tissue necrosis, and decrease in infarct size, preventing or treating toxemia in pregnancy, preventing or reducing platelet loss during extracorporeal circulation, potentiating diuretic-induced diuresis, preventing or reducing adverse reactions to protamine, preventing thrombosis and adverse reactions to radiographic contrast agents, preventing or reducing venous thrombosis (in conjunction with heparin), treating burn injury and promoting wound healing, treating ischemia (alone or in combination with a calcium channel blocker), preserving vascular patency and circulation during and following vascular surgery, preventing reperfusion injury after CNS ischemic states like stroke or vascular surgery, treating tardive dyskenesia, treating Raynaud's disease, treating unstable angina, treating purpura fulminarus, and treating thrombotic thrombocytopenia purpura. Furthermore, the compounds of the invention may be useful in the treatment of pulmonary embolism, diabetic retinopathy, and in coronary artery by-pass, renal dialysis, thrombolysis, endarterectomy, acute renal failure, peripheral vascular disease, intermittent claudication, pulmonary hypertension after mitral valve surgery, pulmonary hypertension after intralipid infusion, subarachnoid hemorrhage, treating or preventing complications following organ transplant (particularly cardiac or renal), treating persistent pulmonary hypertension of the newborn, treating tuberculosis and enhancing immune surveillance and promoting antibiotic penetration to sites of infection/abscess.

The compounds of the invention can be administered orally or parenterally to various mammalian species known to be subject to such maladies, e.g., humans, cats, dogs and the like in an effective amount within the dosage range of about 1 to 100 mg/kg, preferably about 1 to 50 mg/kg and especially about 2 to 25 mg/kg (or from about 5 to about 2500 mg, preferably from about 10 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I or in topical form for wound healing (0.01 to 5% by weight compound of formula I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

4-[3-[(4-Chlorophenyl)sulfonyl]propyl]-phenoxyacetic acid, methyl ester

A.
Dimethyl[4-(2-bromoethyl)phenoxy]-(1,1,2-trimethylpropyl)silane

To a 0° C. solution of 19.7 g (75 mmol) in 350 mL of toluene was added dropwise over 5 minutes 3.8 mL (74 mmol) of bromine. This was stirred for 50 minutes at which time a solution of 21.0 g (75 mmol) of dimethyl [2-(hydroxy)ethylphenoxy] (1,1,2-trimethylpropyl) silane and 6.1 mL (75 mmol) of pyridine in 100 mL of toluene was added dropwise over 10 minutes. The reaction mixture was allowed to warm slowly to 18° C. over 4.3 hours. The mixture was cooled to 0° C. and diluted with 500 mL hexane. The solids were removed by filtration and the filtrate was concentrated in vacuo. The residue was diluted with 500 mL hexane, chilled and passed through a silica gel column. Elution with hexane gave 11.7 g of pure title A bromide.

B.
Dimethyl[4-[3-[(4-chlorophenyl)sulfonyl]propyl]-phenoxy]-(1,1,2-trimethylpropyl)silane To a 0° C. solution of 2.06 g of p-chlorophenyl methyl sulfone (10.8 mmol) in 50 mL of tetrahydrofuran (THF) was added 4.3 mL of 2.5 M n-butyllithium over 2 min. After stirring an additional 35 min at 0° C., the reaction mixture was cooled to −78° C. and a solution of 3.7 g (10.8 mmol) Part A bromide in 10 mL of THF was added. The reaction mixture was allowed to warm to room temperature and stirred overnight. The reaction mixture was partitioned between 100 mL each of saturated $NH_4Cl$ and ethyl ether. The aqueous layer was extracted with 50 mL of ether. The combined ether layers was dried over $MgSO_4$, filtered and concentrated in vacuo to give 4.8 g crude product. Chromatography on 60 g silica gel using 4:1 hexane-ether as eluent afforded 2.6 g (53%) of title sulfone and 1.04 g (13%) dialkylated product.

C. 4-[3-[(4-Chlorophenyl)sulfonyl]propyl]phenol

To a solution of 2.4 g of Part B sulfone in 50 mL of methanol was added 0.5 mL of concentrated HCl. After 1 hour the TLC indicated very little hydrolysis. To the reaction mixture was then added 4 mL of 15% NaOH solution, 5 mL of $H_2O$, 5 mL of THF and 30 mL of ethanol. This was stirred at room temperature for 48 hours. After concentration in vacuo, the reaction mixture was partitioned between 50 mL each of 1 N HCl and ethyl acetate. The aqueous layer was extracted with 2×50 mL of $CHCl_3$. The combined organics was dried over $MgSO_4$, filtered and concentrated in vacuo to afford a white solid. This was triturated with 100 mL of hexane. The solid was collected and dried to give 1.53 g of title sulfone (93%).

D.
4-[3-[(4-Chlorophenyl)sulfonyl]propyl]phenoxyacetic acid, methyl ester To a 0° C. solution of 610 mg of Part C sulfone (1.97 mmol) in 50 mL of THF was added 230 mg of potassium t-butoxide (2.07 mmol). This solution was stirred for 15 min and then 0.3 mL of methyl bromoacetate (3.2 mmol) was added. After 10 min the reaction mixture was allowed to warm to room temperature and an additional 0.2 mL of methyl bromoacetate was added. This was stirred for 70 min at room temperature and then concentrated in vacuo. The residue was partitioned between 20 mL each of 0.25 N HCl and $CH_2Cl_2$. The aqueous layer was extracted with 20 mL of $CH_2Cl_2$. The combined $CH_2Cl_2$ extracts was washed with 10 mL of 0.3 N NaOH, dried over $MgSO_4$, filtered and concentrated in vacuo to give 0.77 g of crude title ester.

EXAMPLE 2
4-[3-[(4-Chlorophenyl)sulfonyl]propyl]phenoxyacetic Acid

To a solution of the Example 1 ester in 25 mL of THF was added 2.0 mL of $H_2O$ and 4.0 mL of 1 N LiOH. This mixture was stirred for 4 hours at which time TLC indicated the reaction to be complete. The reaction mixture was partitioned between 25 mL brine, 1 mL of 6 N HCl, and 10 mL of ethyl acetate. The aqueous layer was extracted with 2×25 mL $CHCl_3$. The combined organics was dried over $MgSO_4$, filtered and concentrated in vacuo. The crude acid was purified by chromatography (16 g silica, 4% $CH_3OH$-$CH_2Cl_2$) followed by recrystallization from $CHCl_3$-hexane to afford 0.44 g of title compound (61% from Example 1 Part B sulfone); m.p.=159°-160.5° C.

EXAMPLE 3
4-[2-[(4-Methoxyphenylsulfonyl]ethyl]phenoxyacetic Acid

A.
Dimethyl[4-[2-[(4-methoxyphenyl)thio]ethyl]phenoxy]-(1,1,2-trimethylpropyl)silane To a solution of p-methoxybenzenethiol (394 mg, 2.80 mmol) in THF (30 ml) is added potassium tert-butoxide (315 mg, 2.80 mmol). After 10 minutes, Example 1 Part A bromide (874 mg, 2.55 mmol), dissolved in THF (5 ml), is added dropwise. After 1 hour, the reaction is diluted with 1N NaOH (20 ml) and then extracted with ether (3×50 ml). The combined organic phases are dried ($Na_2SO_4$) and concentrated in vacuo. Chromatography (ethyl acetate/hexanes) yields title compound.

B.
Dimethyl[4-[2-[(4-methoxyphenyl)sulfonyl]ethyl]-phenoxy]ethanol

To a 0° C. solution of Part A sulfide (200 mg, 0.605 mmol) in methanol (3.5 mL) and THF (3.5 ml) is added a solution of Oxone ® (558 mg, 1.82 mmol of potassium hydrogen persulfate) in water (3.5 ml). After stirring for 40 minutes, the reaction is diluted with water (20 ml) and then extracted with chloroform (3×20 ml). The combined organic layers are dried ($Na_2SO_4$) and concentrated in vacuo. Chromatography (ethyl acetate/hexanes) yields title compound.

C.
4-[2-[(4-Methoxyphenylsulfonyl]ethyl]phenoxyacetic acid

Following the procedure of Examples 1 and 2 except substituting the above Part B sulfone for the Example 1 Part B sulfone the title compound is obtained.

EXAMPLE 4
N-[4-[3-[(4-Chlorophenyl)sulfonyl]propyl]phenoxyacetyl]benzene sulfonamide To a stirred mixture of 1-(3-dimethylaminopropyl)-3-ethylcarbodiimide (1.0 mmol) and 4-dimethylaminopyridine (0.1 mmol) in 8 ml of dimethylformamide is added 1.0 mmol of benzene sulfonamide and 2.0 mmol of triethylamine followed by 1.0 mmol of Example 2 title acid. This mixture is stirred at room temperature for 48 hours and concentrated in vacuo. The residue is partitioned between water and ethyl acetate. The aqueous layer is acidified and extracted with ethyl acetate. Combined ethyl acetate layers are dried, filtered and concentrated in vacuo to afford title sulfonamide.

EXAMPLE 5
5-[4-[3-[(4-Chlorophenyl)sulfonyl]propyl]phenoxymethyl]-1H-tetrazole

A.
4-[3-(4-Chlorophenyl)sulfonyl]propyl]phenoxyacetonitrile

To a 0° C. solution of 1.0 mmol of potassium tert-butoxide in 10 ml of THF is added 1.0 mmol of Example 1, Part C phenol. The reaction mixture is stirred for 1 hour and then 2.0 mmol of bromoacetonitrile is added. The reaction mixture is allowed to warm to room temperature over 2 hours and then is quenched by dilution with saturated aqueous $NaHCO_3$. This is extracted with ethyl acetate. The ethyl acetate extracts are dried, filtered and concentrated in vacuo to afford the crude product. Purification on silica gel using ethyl acetate/hexanes mixtures gives title nitrile.

B.
5-[4-[3-[(4-Chlorophenyl)sulfonyl]propyl]phenoxymethyl-1H-tetrazole A mixture of 1.0 mmol Part A nitrile, 0.2 mmol ammonium chloride and 2 mmol of sodium azide in 5 ml of DMF is heated to 120° C. for 8 hours. The mixture is concentrated in vacuo. The residue is partitioned between 1N HCl and ethyl acetate. The aqueous layer is extracted with ethyl acetate. The combined ethyl acetate layers are dried, filtered and concentrated in vacuo. Purification on silica gel using $CH_3OH/CH_2Cl_2$ mixture affords title tetrazole.

EXAMPLES 6 to 18

Following the procedures of Examples 1 and 2, except substituting for Example 1 part A bromide the bromoalkyl benzene compound shown in Column II of Table I set out below and substituting for (p-chlorophenyl)methylsulfone the sulfone shown in Column I, and substituting for methylbromoacetate the alkylating agent shown in Column III, the product shown in Column IV is obtained.

It will be appreciated that wherein the Ar group in the starting materials shown in Column I includes substituents that include acidic hydrogens such as OH or primary or secondary amine then these starting materials will be reacted with a protecting compound such as set out hereinbefore with respect to "Pro" and the Pro group will be removed as a final step as described above.

| Ex. No. | Column I<br>$Ar-\overset{O}{\underset{O}{S}}-CH_3$<br>Ar | $Br-(CH_2)_{p-1}$<br>$(CH_2)_{p-1}$ | Column II<br>O-Protecting group<br>(position)-O-Protecting group | Column III<br>$Br(CH_2)_m-COOCH_3$<br>$(CH_2)_m$ | Column IV<br>$Ar-\overset{O}{\underset{O}{S}}-CH_2-(CH_2)_{p-1}$<br>Ar | $O-(CH_2)_m-COOH$<br>$(CH_2)_{p-1}$ (position)-$(CH_2)_m-$ |
|---|---|---|---|---|---|---|
| 6. | phenyl | $-CH_2-\overset{CH_3}{\underset{}{CH}}-$ | (4)- | $CH_2$ | Same as Col. I | same as Col. II and III |
| 7. | naphthyl | $-CH_2-CH_2-$ | (3)- | $-CH_2-\overset{CH_3}{\underset{}{CH}}-$ | | |
| 8. | 4-F-phenyl | $-CH_2-\overset{H}{\underset{CH_3}{C}}-CH_2-$ | | $CH_2$ | | |
| 9. | 4-HO-phenyl | $-CH_2-\overset{C_2H_5}{\underset{}{CH}}-$ | (4)- | $-CH_2-CH_2-$ | | |
| 10. | 4-CH$_3$O-phenyl | $-CH_2-CH_2-\overset{CH_3}{\underset{}{CH}}-CH_2-$ | (4)- | $-CH_2-$ | | |
| 11. | 6-CH$_3$-naphthyl | $-CH_2-\overset{CH_3}{\underset{}{CH}}-$ | (3)- | $-(CH_2)_3-$ | | |
| 12. | 4-phenyl-phenyl | $-CH_2-\overset{OCH_3}{\underset{}{CH}}-$ | (2)- | $-(CH_2)_4-$ | | |

-continued

| Ex. No. | Column I<br>$Ar-\overset{O}{\underset{O}{S}}-CH_3$<br>Ar | Column II<br>$Br-(CH_2)_{p-1}-\underset{1}{\overset{2}{\bigcirc}}\overset{3}{\underset{}{\bigcirc}}\overset{4}{\text{O-Protecting group}}$<br>$(CH_2)_{p-1}$ (position)-O-Protecting group | Column III<br>$Br(CH_2)_m-COOCH_3$<br>$(CH_2)_m$ | Column IV<br>$Ar-\overset{O}{\underset{O}{S}}-CH_2-(CH_2)_{p-1}-\underset{}{\bigcirc}-O-(CH_2)_m-COOH$<br>Ar $(CH_2)_{p-1}$ (position)-$(CH_2)_m$ |
|---|---|---|---|---|
| 13. | ⟨C₄H₉-phenyl⟩ | —(CH₂)₃— | (4)- | —CH₂— |
| 14. | ⟨CH₃O-biphenyl⟩ | —CH₂—CH₂—CH— $\overset{|}{CH_3}$ | (4)- | —CH₂CH₂— |
| 15. | ⟨CH₃—NH-phenyl⟩ | —CH₂— | (3)- | —(CH₂)₃— | Same as Col. I | Same as Col. II and III |
| 16. | ⟨C₃H₇-phenyl⟩ | —CH₂— | (4)- | $\overset{CH_3}{\underset{}{-CH-}}$ |
| 17. | ⟨C₂H₅NH-phenyl⟩ | —CH₂—CH₂— | (3)- | —CH₂—CH—CH₂— $\overset{|}{CH_3}$ |
| 18. | ⟨phenyl⟩ | —(CH₂)₅— | (2)- | —CH₂— |

EXAMPLES 19 to 30

Following the procedure of Example 3 except substituting for p-methoxybenzenethiol, the mercaptan shown in Column I of Table II set out below and substituting for the bromoalkylenebenzene compound, the compound shown in Column 11, the protected sulfone shown in Column III is produced which may be used to prepare compounds in accordance with the present invention.

| Ex. No. | Column I<br>Ar—SH<br>Ar | Column II<br>Br—(CH$_2$)$_p$—[O-Protecting Group]<br>(CH$_2$)$_p$ | (position)-O-Protecting group | Column III<br>Ar—S—(CH$_2$)$_p$—[O-Protecting group]<br>Ar | (CH$_2$)$_p$ | (position)-O-Protecting group |
|---|---|---|---|---|---|---|
| 19. | phenyl | —CH$_2$—CH(CH$_3$)— | (4)- | Same as Col. I | Same as Col. II | Same as Col. II |
| 20. | naphthyl | —CH$_2$—CH$_2$— | (3)- | | | |
| 21. | 4-fluorophenyl | —CH$_2$—C(H)(CH$_3$)—CH(CH$_3$)— | (2)- | | | |
| 22. | 3-hydroxyphenyl | —CH(C$_2$H$_5$)— | (4)- | | | |
| 23. | 4-methoxyphenyl | —CH$_2$—CH$_2$—CH(CH$_3$)—CH$_2$— | (4)- | | | |
| 24. | 6-methylnaphthyl | —CH(CH$_3$)—CH(CH$_3$)— | (3)- | | | |
| 25. | 4-phenylphenyl | —CH$_2$—CH(OCH$_3$)— | (2)- | | | |

-continued

| Ex. No. | Column I<br>Ar—SH<br>Ar | Column II<br>(CH$_2$)$_p$ | (position)-O-Protecting Group | Column III<br>Ar—S—(CH$_2$)$_p$<br>Ar · (CH$_2$)$_p$ · (position)-O-Protecting group |
|---|---|---|---|---|
| 26. | 4-CH$_3$-C(=O)-phenyl | —(CH$_2$)$_3$— | (4)- | |
| 27. | 4-C$_6$H$_5$-C(=O)-phenyl | —CH$_2$—CH$_2$—CH(CH$_3$)— | (3)- | |
| 28. | 4-CH$_3$NH-phenyl | —CH$_2$— | (4)- | |
| 29. | 4-CH$_3$-C(=O)-phenyl | —CH$_2$— | (3)- | |
| 30. | 4-Br-phenyl | —CH$_2$— | (2)- | |

What is claimed is:

1. A compound having the structure

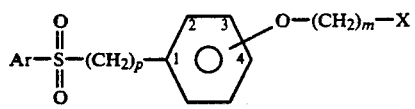

wherein
Ar is an aryl group which is unsubstituted or substituted with one, two or three of halogen, lower alkyl, lower alkoxy, phenyl, hydroxy, alkanoyl, aroyl, alkylamino, alkoxycarbonyl or carboxy;

X is COOR wherein R is hydrogen, alkali metal, lower alkyl or X is 5-tetrazolyl or

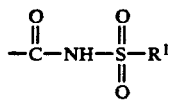

wherein $R^1$ is lower alkyl or aryl
p is 1 to 5;
m is 1 to 4;
and the $(CH_2)_m$ and $(CH_2)_p$ groups may be unsubstituted or optionally substituted with one or two lower alkyl groups and/or are one or two lower alkoxy groups.

2. The compound as defined in claim 1 wherein X is COOR and R is H.

3. The compound as defined in claim 1 wherein X is 5-tetrazolyl.

4. The compound as defined in claim 1 wherein X is

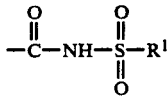

5. The compound as defined in claim 1 wherein Ar is halosubstituted phenyl, p is 2 to 4, m is 1 to 3 and X is COOR.

6. The compound as defined in claim 1 having the name 4-[3-[(4-chlorophenyl)sulfonyl]propyl]phenoxyacetic acid or its methyl ester.

7. A composition for inhibiting arachidonic acid-induced platelet aggregation and bronchoconstriction comprising an effective amount of a compound as defined in claim 1 or a pharmaceutially acceptable salt thereof, and a pharmaceutically acceptable carrier therefor.

* * * * *